(12) United States Patent
Yan et al.

(10) Patent No.: US 11,660,405 B2
(45) Date of Patent: May 30, 2023

(54) ELECTRONIC CIGARETTE AND METHOD THEREOF

(71) Applicant: Shenzhen First Union Technology Co., Ltd., Shenzhen (CN)

(72) Inventors: Huiyong Yan, Shenzhen (CN); Yonghai Li, Shenzhen (CN); Zhongli Xu, Shenzhen (CN)

(73) Assignee: Shenzhen First Union Technology Co., Ltd., Guangdong Province (CN)

(*) Notice: Subject to any disclaimer, the term of this patent is extended or adjusted under 35 U.S.C. 154(b) by 657 days.

(21) Appl. No.: 16/443,894

(22) Filed: Jun. 18, 2019

(65) Prior Publication Data

US 2019/0387794 A1 Dec. 26, 2019

(30) Foreign Application Priority Data

Jun. 20, 2018 (CN) .......................... 201810639825.6

(51) Int. Cl.
*A24F 47/00* (2020.01)
*A61M 11/04* (2006.01)
*G01L 9/00* (2006.01)
*H01M 10/48* (2006.01)
*A24F 40/51* (2020.01)
*A24F 40/60* (2020.01)
*A24F 40/10* (2020.01)

(52) U.S. Cl.
CPC .......... *A61M 11/042* (2014.02); *A24F 40/51* (2020.01); *A24F 40/60* (2020.01); *G01L 9/0041* (2013.01); *H01M 10/488* (2013.01); *A24F 40/10* (2020.01); *H01M 2220/30* (2013.01)

(58) Field of Classification Search
CPC .... A24F 47/002; A24F 47/004; A24F 47/006; A24F 47/008; A24F 42/10
See application file for complete search history.

(56) References Cited

U.S. PATENT DOCUMENTS

| 2014/0096781 A1* | 4/2014 | Sears | A24F 40/00 |
| | | | 131/328 |
| 2014/0096782 A1* | 4/2014 | Ampolini | A24F 40/60 |
| | | | 131/328 |
| 2014/0270727 A1* | 9/2014 | Ampolini | A24F 40/50 |
| | | | 392/387 |

(Continued)

FOREIGN PATENT DOCUMENTS

CN 107 280 072 A 10/2017

*Primary Examiner* — Hai Phan
*Assistant Examiner* — Son M Tang
(74) *Attorney, Agent, or Firm* — PROI Intellectual Property US; Klaus Michael Schmid

(57) ABSTRACT

An electronic cigarette and a method of controlling the electronic cigarette are disclosed, the electronic cigarette includes a controller; and at least one air pressure sensor coupled with the controller; the at least one air pressure sensor is configured for detecting a first air pressure in an air flow path of the electronic cigarette and a second air pressure of an ambient atmosphere where the electronic cigarette is located, and sending the first air pressure and the second air pressure to the controller; the controller is configured for receiving the second air pressure and the first air pressure and controlling an atomizer to be on or off based on a pressure differential between the first air pressure and the second air pressure.

7 Claims, 10 Drawing Sheets

(56) References Cited

U.S. PATENT DOCUMENTS

| | | | |
|---|---|---|---|
| 2015/0068523 A1* | 3/2015 | Powers | A24F 40/70 128/203.14 |
| 2015/0245658 A1 | 9/2015 | Worm et al. | |
| 2015/0313284 A1* | 11/2015 | Liu | A24F 40/57 219/490 |
| 2016/0128389 A1* | 5/2016 | Lamb | G01L 9/0052 131/328 |
| 2016/0360785 A1* | 12/2016 | Bless | A24F 40/53 |
| 2017/0245547 A1 | 8/2017 | Lipowicz | |
| 2018/0206552 A1* | 7/2018 | Sebastian | A24F 40/485 |
| 2018/0325183 A1* | 11/2018 | Huang | G01F 1/6845 |
| 2018/0360117 A1* | 12/2018 | Yan | G05B 19/416 |
| 2019/0289908 A1* | 9/2019 | Worm | A24F 40/46 |
| 2019/0387794 A1* | 12/2019 | Yan | H01M 10/488 |
| 2021/0145072 A1* | 5/2021 | Mullin | A24F 40/53 |
| 2022/0175026 A1* | 6/2022 | Mo | A24F 40/10 |

* cited by examiner

ELECTRONIC CIGARETTE AND METHOD THEREOF

CROSS REFERENCE TO RELATED APPLICATIONS

The present application claims priority to Chinese Patent Application CN201810639825.6 filed on Jun. 20, 2018 and Chinese Patent Application CN201811329295.1 filed on Nov. 9, 2018, which are hereby incorporated by reference herein as if set forth in its entirety.

TECHNICAL FIELD

The present disclosure relates to the field of cigarette articles, and particularly, to an electronic cigarette.

BACKGROUND ART

An electronic cigarette as an electronic product simulating traditional cigarettes has a same appearance, aerosol, taste and feeling with the real cigarettes. By relying on vaporization of tobacco liquid, the tobacco liquid containing nicotine etc. becomes an aerosol drawn by the user later on. Since the electronic cigarette is portable, immune from open flames and environmental friendly, the electronic cigarette attracts an abundance of smokers.

The electronic cigarette generally includes an atomizer, a power supply set and a control unit, the atomizer heats the tobacco liquid upon provided with electricity, to generate an aerosol for users to draw out. The power supply set is configured for supplying power to the atomizer, the control unit is configured for controlling on or off state of the atomizer. The prior art control unit in the electronic cigarette includes a button pressed type and an induction auto-start type. Currently, the induction auto-start electronic cigarette takes increasingly high market share.

For the induction auto-start electronic cigarette, the control unit thereof generally includes a controller and a sensor. An elastic membrane is installed in the sensor, one side of the elastic membrane is in communication with an air flow path in the electronic cigarette, an opposite side of the elastic membrane is in communication with ambient atmosphere, when the user puffs on the electronic cigarette, an air pressure within the air flow path is lower than that of the ambient atmosphere, enabling the side of the elastic membrane in communication with ambient atmosphere suffers greater pressure than the opposite side thereof in communication with the air flow path of the electronic cigarette, as a result, the elastic membrane elastically deforms causing a capacitance of the sensor to be changed, as well the changed signal is sent to the controller. The controller controls the atomizer to start.

However, when the leaking tobacco liquid stored in the atomizer or condensed aerosol reach the sensor, the capacitance of the sensor may be changed, enabling the controller to control the start-up of the atomizer, that is, the electronic cigarette is initiated automatically.

SUMMARY

To overcome the above drawbacks, the present disclosure generally relates to an electronic cigarette, which avoids leaking tobacco liquid or condensed aerosol to reach the sensor causing the electronic cigarette is initiated automatically.

According to embodiments of the present disclosure, an electronic cigarette is disclosed including a controller and at least one air pressure sensor coupled with the controller;

the at least one air pressure sensor configured for detecting a first air pressure within an air flow path of the electronic cigarette and a second air pressure in the ambient atmosphere where the electronic cigarette is located, and sending the first air pressure and the second air pressure to the controller;

the controller configured for receiving the second air pressure and the first air pressure and controlling an atomizer to be on/off based on a pressure differential between the second air pressure and the first air pressure;

As used herein, the electronic cigarette includes a first air pressure sensor and a second air pressure sensor respectively coupled with the controller;

the first air pressure sensor being arranged within an air flow path of the electronic cigarette and configured for detecting a first air pressure within the air flow path and sending the first air pressure to the controller;

the second air pressure sensor arranged at a position that is in communication with ambient atmosphere, and configured for detecting a second air pressure of the ambient atmosphere and sending the second air pressure to the controller;

Optionally, the electronic cigarette includes one air pressure sensor coupled with the controller, the air pressure sensor includes a first channel and a second channel, a first sensing surface arranged within the first channel and a second sensing surface arranged within the second channel;

the first channel in communication with an air flow path of the electronic cigarette such that the first sensing surface contacts airflow in the air flow path to detect the first air pressure; the second channel in communication with ambient atmosphere of the electronic cigarette such that the second sensing surface contacts the ambient atmosphere of the electronic cigarette to detect the second air pressure.

As used herein, the controller includes a threshold value, configured as: when the pressure differential is larger than the threshold value controlling the atomizer to be initiated, and when the pressure differential is less than or equal to the threshold value controlling the atomizer not to be initiated or to be closed.

As used herein, the electronic cigarette further includes a power control circuit coupled with the controller; when the atomizer is initiated, the controller defines a real-time output power corresponding to the detected pressure differential according to a corresponding relationship between the pressure differentials and the real-time output powers, and sending an instruction to the power control circuit, afterwards the power control circuit in response to the instruction outputs the real-time output power to the atomizer.

As used herein, in the corresponding relationship between pressure differentials and output powers, the greater pressure differential is corresponding to the greater real-time output power.

As used herein, the pressure differential is equal to that the second air pressure deducts the first air pressure; the controller is configured as: when the pressure differential is more than zero, determining an airflow in the air flow path is flowing outside from an aerosol outlet with consequently controlling the atomizer to be initiated; when the pressure differential is less than zero, determining an airflow in the air flow path is flowing inside from the aerosol outlet with consequently controlling the atomizer not to be initiated or to be closed.

Optionally, the air pressure sensor including a first measuring membrane and a second measuring membrane; a chamber formed between the first measuring membrane and the second measuring membrane; the first sensing surface arranged on a first side of the first measuring membrane outside the chamber; the second sensing arranged on a second side of the second measuring membrane outside the chamber.

As used herein, the electronic cigarette further includes a power supply set having a rechargeable battery and a power reminder unit coupled with the controller; when the rechargeable battery runs out of charge, the power reminder unit is capable of reminding for supplying power to the rechargeable battery.

As used herein, the power reminder unit is an indicator light, when the rechargeable battery runs at different reminding capacities, the controller is capable of controlling the indicator light to generate different colors.

Another embodiment of the present disclosure provides an electronic cigarette, the electronic cigarette includes a controller; one air pressure sensor coupled with the controller; the air pressure sensor comprising a first channel, a second channel, a first sensing surface arranged within the first channel and a second sensing surface arranged within the second channel;

the first channel in communication with the air flow path, enabling the first sensing surface to contact an airflow in the air flow path via the first channel, to detect the first air pressure in the air flow path; the second channel in communication with the ambient atmosphere of the electronic cigarette, enabling the second sensing surface to contact the ambient atmosphere of the electronic cigarette via the second channel, to detect the second air pressure in the ambient atmosphere; and the air pressure sensor feeding back the pressure differential between the second air pressure and the first air pressure to the controller; the controller capable of controlling on/off state of the atomizer according to the pressure differential As used herein, the air pressure sensor includes a measuring membrane, the first sensing surface and the second sensing surface are respectively disposed at two sides of the measuring membrane; axes of the first channel and the second channel are both perpendicular to a panel surface of the measuring membrane.

A method is disclosed by the present disclosure, the method includes: detecting a first air pressure in an air flow path of an electronic cigarette via a first air pressure sensor; detecting a second air pressure in an ambient atmosphere of the electronic cigarette via a second air pressure sensor; as used herein, the first air pressure sensor is arranged in the air flow path of the electronic cigarette; the second air pressure sensor is arranged in a position of the electronic cigarette where is in communication with the ambient atmosphere;

determining whether the pressure differential of the second air pressure deducting the first air pressure is greater than zero;

if the pressure differential is greater than zero, further determining whether the pressure differential is greater than a preset threshold value;

if the pressure differential is greater than the preset threshold value, initiating the atomizer in the electronic cigarette;

if the pressure differential is less than zero, or the pressure differential is more than zero, less than or equal to the preset threshold value, failing to initiate or closing the atomizer in the electronic cigarette.

Optionally, after a step of if the pressure differential is greater than the preset threshold value, initiating the atomizer in the electronic cigarette, the method further includes:

after initiating the atomizer, determining a real-time output power based on the detected pressure differential according to a corresponding relationship between stored pressure differentials and the output powers;

outputting the real-time output power that is corresponding to the pressure differential to the atomizer, such that the atomizer generates a certain amount of aerosol that is corresponding to the real-time output power.

Compared to the prior art, the air pressure sensor in the present disclosure is provided with a first sensing surface and a second sensing surface, by relying on the first sensing surface detecting a first air pressure in the air flow path, by replying on the second sensing surface detecting a second air pressure in the ambient atmosphere; the controller receives the first air pressure and the second air pressure, further controls the atomizer to be initiated or be closed according to a pressure differential that equals to the second air pressure deducts the first air pressure, which avoids the leaking tobacco liquid or condensed aerosol to reach the air pressure sensor causing the electronic cigarette to be initiated automatically, ensuring a good user experience.

Advantages of the present disclosure is, the electronic cigarette in the present disclosure includes a controller, a first air pressure and a second air pressure that are both coupled with the controller. As used herein, the second air pressure sensor is arranged at a position of the electronic cigarette where is in communication with ambient atmosphere, configured to detect a second air pressure, further sending the second air pressure to the controller; the first air pressure sensor is arranged in the air flow path of the electronic cigarette to detect the first air pressure in the air flow path and sending the first air pressure to the controller. The controller is configured to control the start or close of the atomizer according to the pressure differential between the second air pressure and the first air pressure. Since the controller controls the start or close of the atomizer according to the pressure differential, which is the second air pressure deducts the first air pressure, the pressure differential is consistent and controllable, can't be affected by the tobacco liquid or condensed aerosol. In this way, the sensibility of the electronic cigarette is consistent and reliable, without false triggering or out of service.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

Figure 1:
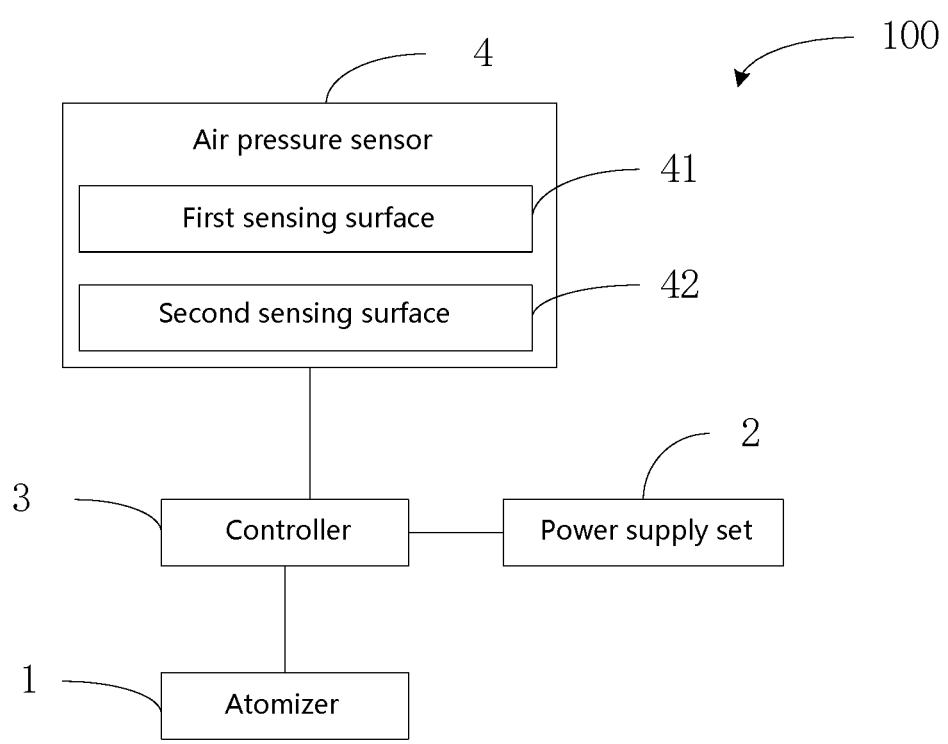
FIG. 1 is a block diagram of the electronic cigarette according to a first embodiment of the present disclosure.

Numerals indicating components are illustrated herein:

| Electronic cigarette 100 | Atomizer 1 | Air flow path 10 | Aerosol outlet 11 |
|---|---|---|---|
| Air inlet 12 | Cartridge 13 | Power supply set 2 | Controller 3 |
| Air pressure sensor 4 | First sensing surface 41 | Second sensing surface 42 | A first channel 43 |
| A second channel 44 | Measuring membrane 45 | First measuring membrane 46 | Second measuring membrane 47 |
| Chamber 48 | Power reminder unit 5 | Power control unit 6 | |
| Battery management circuit 7 | | | |

DETAILED DESCRIPTION

Provided herein are an electronic cigarette simulating traditional cigarette in same appearance and same taste. By replying on atomization, the tobacco liquid containing nicotine is vaporized as an aerosol drawn by the users.

In general, the electronic cigarette mainly includes a reservoir for holding nicotine solution, a vapor (atomizer) and a power supply set. Upon the atomizer is supplied with electricity the nicotine solution in the reservoir is transformed to an aerosol. In the prior art, by using an airflow sensor to initiate the atomizer, once the user puffs on/draws the electronic cigarette, the power supply set starts to work supplying power to the atomizer. In other cases, the user can push a button to let the power supply set supply power to the atomizer, then the user can draw smoking. The airflow sensor mostly adopts an inductive airflow sensor which is more convenient to use but has inconsistent sensibility, not easy to control, can't ensure the consistency of the electronic cigarette, once the tobacco liquid and condensed aerosol/water reach it, it is easy to cause false triggering or out of work, which affects the user experience.

Embodiment One

Figure 2:
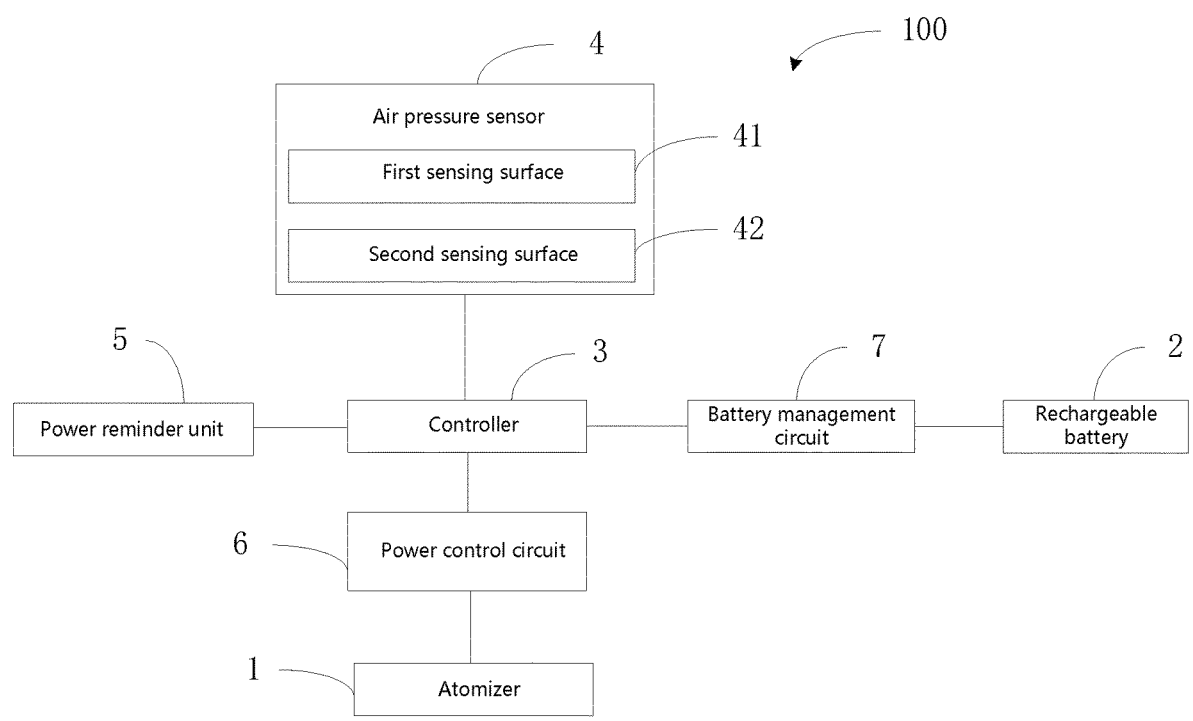
FIG. 2 is a block diagram of the electronic cigarette according to a first embodiment of the present disclosure.

As shown in FIG. 1 and FIG. 2, which are block diagrams of the electronic cigarette 100. The electronic cigarette 100 mainly includes an atomizer 1, a power supply set 2, a controller 3, an air pressure sensor 4, a power reminder unit 5, a power control circuit 6 and a battery management circuit 7.

The atomizer 1 is configured to hold tobacco liquid, the atomizer 1 has a cartridge for heating the tobacco liquid to generate an aerosol drawn by the user directly. Upon the cartridge is provided with electricity, the electronic cigarette 100 has an air inlet 12, an aerosol outlet 11 and an air flow path 10 linking the air inlet 12 and the aerosol outlet 11 in a mouthpiece of the cartridge. When the user puffs on the electronic cigarette via the aerosol outlet 11 in the mouthpiece, the aerosol generated by the cartridge is flowing through the air flow path 10, the aerosol outlet 11 to the user's mouth or nasal cavity.

The power supply set 2 is mainly configured for supplying power to the cartridge 13 in the atomizer 1. The power supply set 2 adopts a rechargeable batteries, the electronic cigarette 100 has a charging interface via which the rechargeable batteries may be charged.

The controller 3 is respectively coupled with the atomizer 1 and the power supply set 2. By receiving signals transferred from the air pressure sensor 4, the controller 3 controls the cartridge 13 to be initiated or closed, that is to control the atomizer 1 to be initiated or closed is realized.

Figure 3:
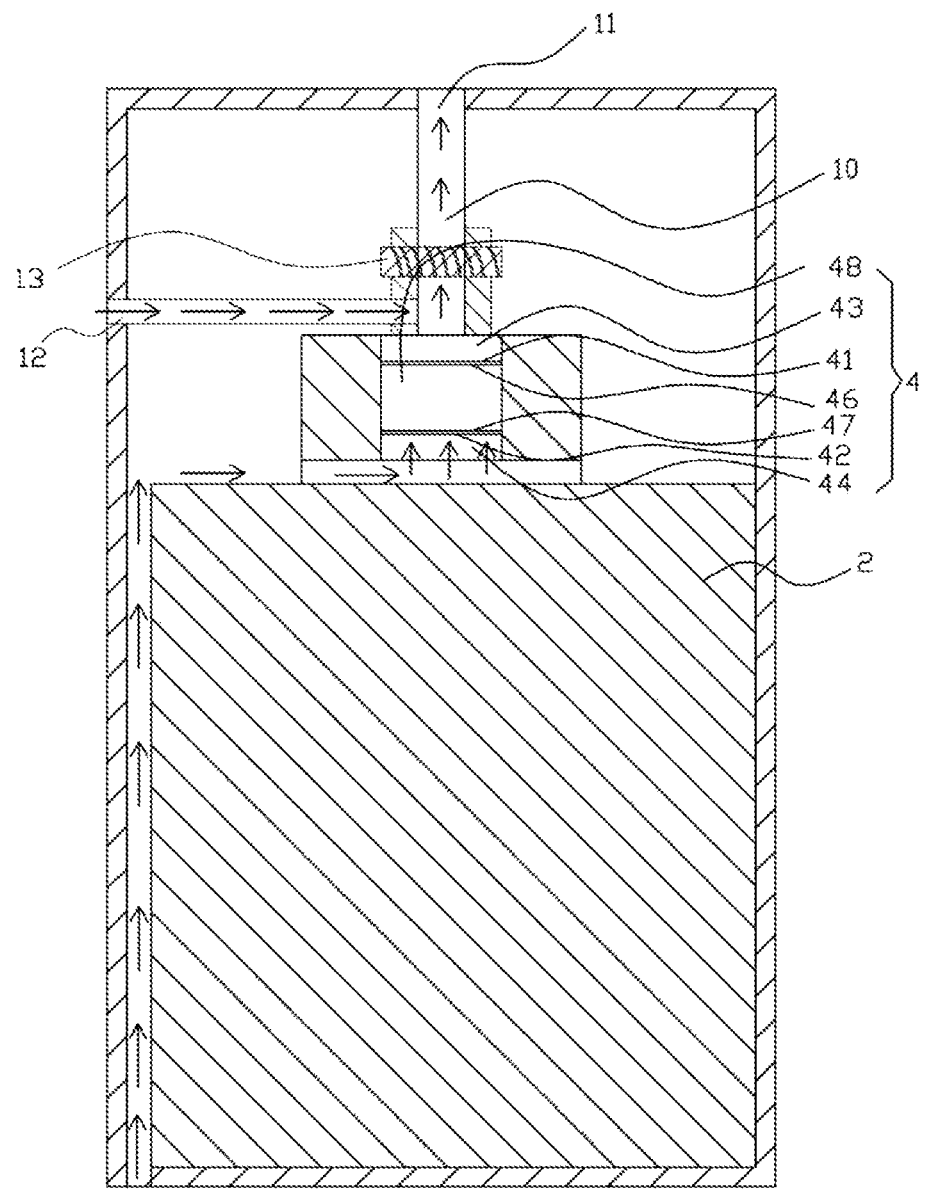
FIG. 3 is a cross-sectional view of the electronic cigarette according to a first embodiment of the present disclosure.

As shown in FIG. 1 to FIG. 3, the air pressure sensor 4 includes a first measuring membrane 46 and a second measuring membrane 47, a panel surface of the first measuring membrane 46 is perpendicular to the panel surface of the second measuring membrane 47. The first measuring membrane 46 and the second measuring membrane 47 encompasses a chamber 48 that is closed, that is, the chamber 48 can't be in communication with the ambient atmosphere. The first sensing surface 41 is disposed on a side of the first measuring membrane 46 in which the side thereof is outside the chamber 48, the second sensing surface 42 is disposed on a side of the second measuring membrane 47 in which the side thereof is outside the chamber 48.

The air pressure sensor 4 is provided with a first channel 43 and a second channel 44, the first channel 43 is in communication with the air flow path 10, the first sensing surface 41 is in contact with the airflow in the air flow path 10 via the first channel 43 to detect the first air pressure in the air flow path 10 and sending the first air pressure to the controller 3. The second channel 44 is in communication with the ambient atmosphere of the electronic cigarette 100, allowing the second sensing surface 42 to contact with the ambient atmosphere via the second channel 44, so as to detect the second pressure, further send the second pressure to the controller 3. The axis of the first channel 43 is perpendicular to the panel surface of the first measuring membrane 46, the axis of the second channel 44 is perpendicular to the panel surface of the second measuring membrane 47.

Understandable, in other embodiments, the axis of the first channel 43 is also perpendicular to the axis of the second channel 44.

The controller 3 is configured for receiving the first air pressure and the second air pressure, and controlling the on/off state of the atomizer 1 according to the first air pressure and the second air pressure. More specifically, the controller 3 has a preset threshold value, when the user puffs on the aerosol outlet 11 of the atomizer 1, the air pressure in the air flow path 10 is basically the same as the ambient atmosphere, which is the first air pressure is equal to the second air pressure. When the user puffs on the aerosol outlet 11 of the atomizer 1, the air in the air flow path 10 is quickly expelled to outside of the atomizer 1 via the aerosol outlet 11, such that the air pressure in the air flow path 10 descends sharply, that is the first air pressure is less than the second air pressure, the controller 3 controls the cartridge 13 to be electrically conducted with the rechargeable battery, the cartridge 13 is powered on to heat the tobacco liquid, so as to generate an aerosol drawn by the user directly.

Understandable, to avoid the electronic cigarette 100 creating a great disturbance in the transport, carriage or other circumstances, the first air pressure in the air flow path 10 is less than the second air pressure in the ambient atmosphere, so that the electronic cigarette 100 is abnormally initiated.

Therefore, a threshold value is defined in the control method, when the pressure differential equal to the second air pressure deducting the first air pressure is greater than the threshold value, the cartridge 13 starts to be powered on to generate heat, when the pressure differential is less than or equal to the threshold value, the controller 3 controls the atomizer 1 not to be initiated or to be closed.

Understandable, the above pressure differential and the threshold value are all positive.

Understandable, when the first air pressure is greater than the second air pressure, the controller 3 controls the atomizer 1 not to be initiated or to be closed. In this circumstance, the user blows the electronic cigarette via the aerosol outlet 11, the controller 3 is capable of determining air is blowing into the air flow path 10 of the electronic cigarette 100.

The power control circuit 6 is coupled with the controller 3. According to the pressure differential between the second air pressure and the first air pressure, the power control circuit 6 is capable of determining a real-time output power. The controller 3 gives instructions to the power control circuit 6, the power control circuit 6 in response to the instructions outputs a real-time output power to the atomizer 1.

Understandable, a greater pressure differential between the second air pressure and the first air pressure is corresponding to a greater output power. If the user tries harder to puff on the electronic cigarette, the air pressure in the air flow path 10 descends more sharply so the pressure differential is bigger, that means, the user needs more aerosol which is more satisfying. In this case, the controller 3 controls the batteries to output greater output power, thus making the cartridge 13 generate more aerosol.

The battery management circuit 7 is coupled with the controller 3, for example, in a process of charging the rechargeable battery, when the remaining capacity of the rechargeable battery is lower than a threshold value, like when the remaining capacity of the rechargeable battery is less than 60%, it is available to charge the rechargeable batteries quickly so as to save the charging time. The controller 3 is capable of sending some instructions to the battery management circuit 7. The battery management circuit 7 in response to the instructions controls the power supply set of the electronic cigarette 100.

The battery reminder unit 5 is coupled with the controller 3 for receiving different instructions from the controller 3 and then responding to such instructions. More specifically, the battery reminder unit 5 is an indicating light. When the capacity of the rechargeable batteries is at different levels, the controller 3 controls the indicating light to generate light of different colors. More specifically, when the remaining capacity of the rechargeable battery is less than 10%, the indicating light generates red light illustrating the capacity of the batteries is depleted. When the remaining capacity of the rechargeable battery is in a range of 10%-30%, the indicating light generates orange light. When the remaining capacity of the rechargeable battery is in a range of 30%-90%, the indicating light generates yellow light. When the remaining capacity of the rechargeable battery is more than 90%, the indicating light generates green light. Based on light of different colors, it is available to obtain remaining capacities of the rechargeable batteries.

Figure 4:
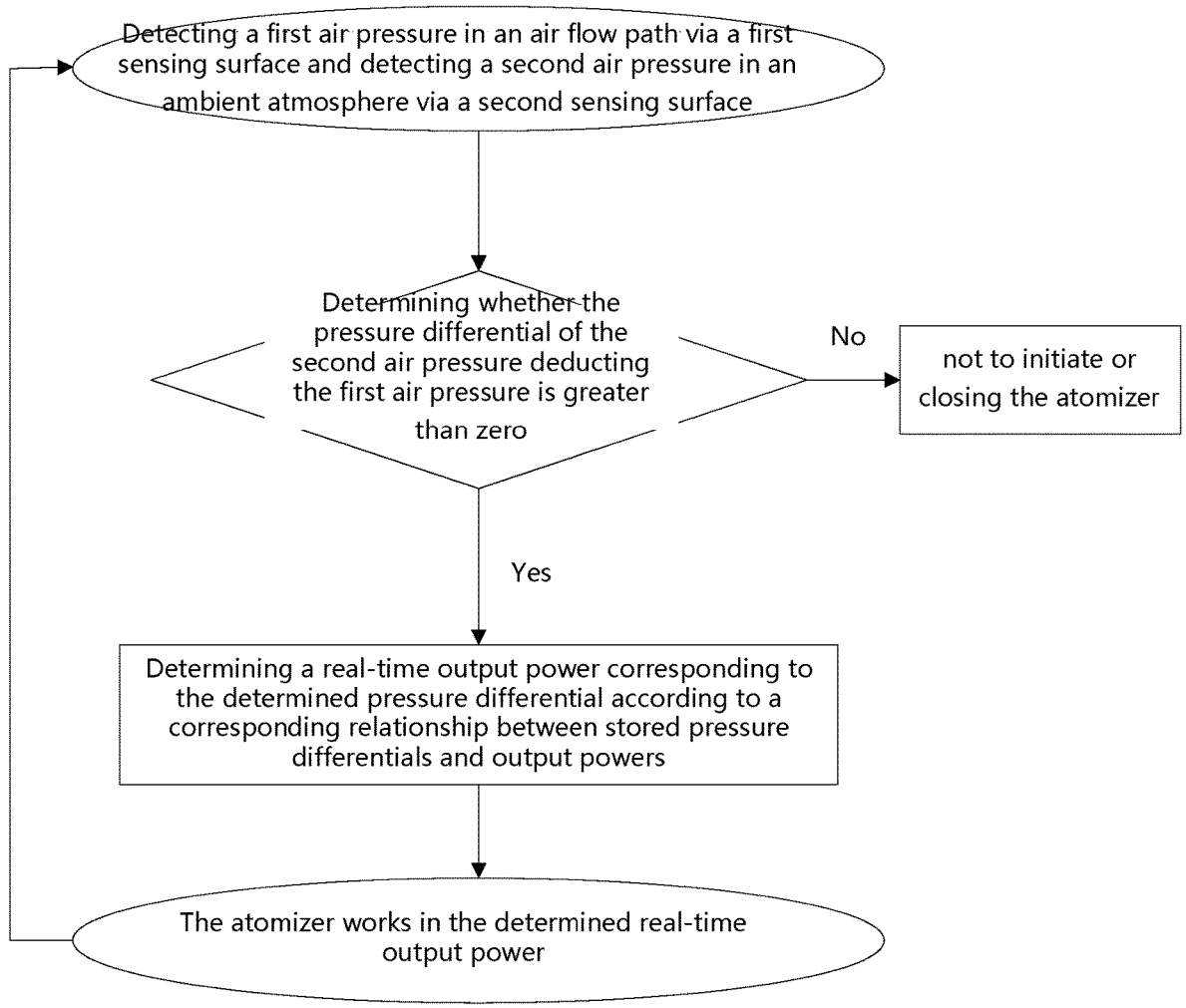
FIG. 4 is a flow chat of the electronic cigarette according to embodiments of the present disclosure.

As shown in FIG. 4, when the user puffs on the mouth piece of the electronic cigarette 100, the first sensing surface 41 of the air pressure sensor 4 detects the first air pressure in the air flow path 10, the second sensing surface 42 detects the second air pressure in the ambient atmosphere. The controller 3 receives the first air pressure and the second air pressure, comparing the pressure differential between the second air pressure and the first air pressure to the threshold value. If the pressure differential is greater than the threshold value, the controller 3 initiates the atomizer 1 and then compares the threshold value to the output power. According to the corresponding relationship between the pressure differential and the output power, the controller 3 controls the atomizer 1 to output the real-time output power corresponding to the pressure differential. If the pressure differential is less than the preset pressure differential in the controller 3, the controller 3 controls the atomizer 1 not to be initiated or to be closed.

The air pressure sensor 4 in the present disclosure has a first sensing surface 41 and a second sensing surface 42. By means of the first sensing surface 41 detecting the first air pressure in the air flow path 10 and the second sensing surface 42 detecting the second air pressure in the ambient atmosphere. The controller 3 receives the first air pressure and the second air pressure, to control the on/off state of the atomizer 1 based on the pressure differential there-between, avoiding that the leaking tobacco liquid or condensed aerosol to reach the air pressure sensor 4 causing the electronic cigarette 100 is initiated automatically, therefore ensuring good user experience.

As described above, according to the detected pressure differential between the second air pressure and the first air pressure, and a stored corresponding relationship between the pressure differentials and the output powers, a real-time output power corresponding to the detected pressure differential is determined. The controller 3 gives an instruction to the power control circuit 6, further the power control circuit 6 in response to the instruction outputs the real-time output power to the atomizer 1. As used herein, the greater pressure differential is corresponding to greater output power, so the electronic cigarette generates more amount of aerosol ensuring the user to get more highly satisfied.

Embodiment Two

Figure 5:
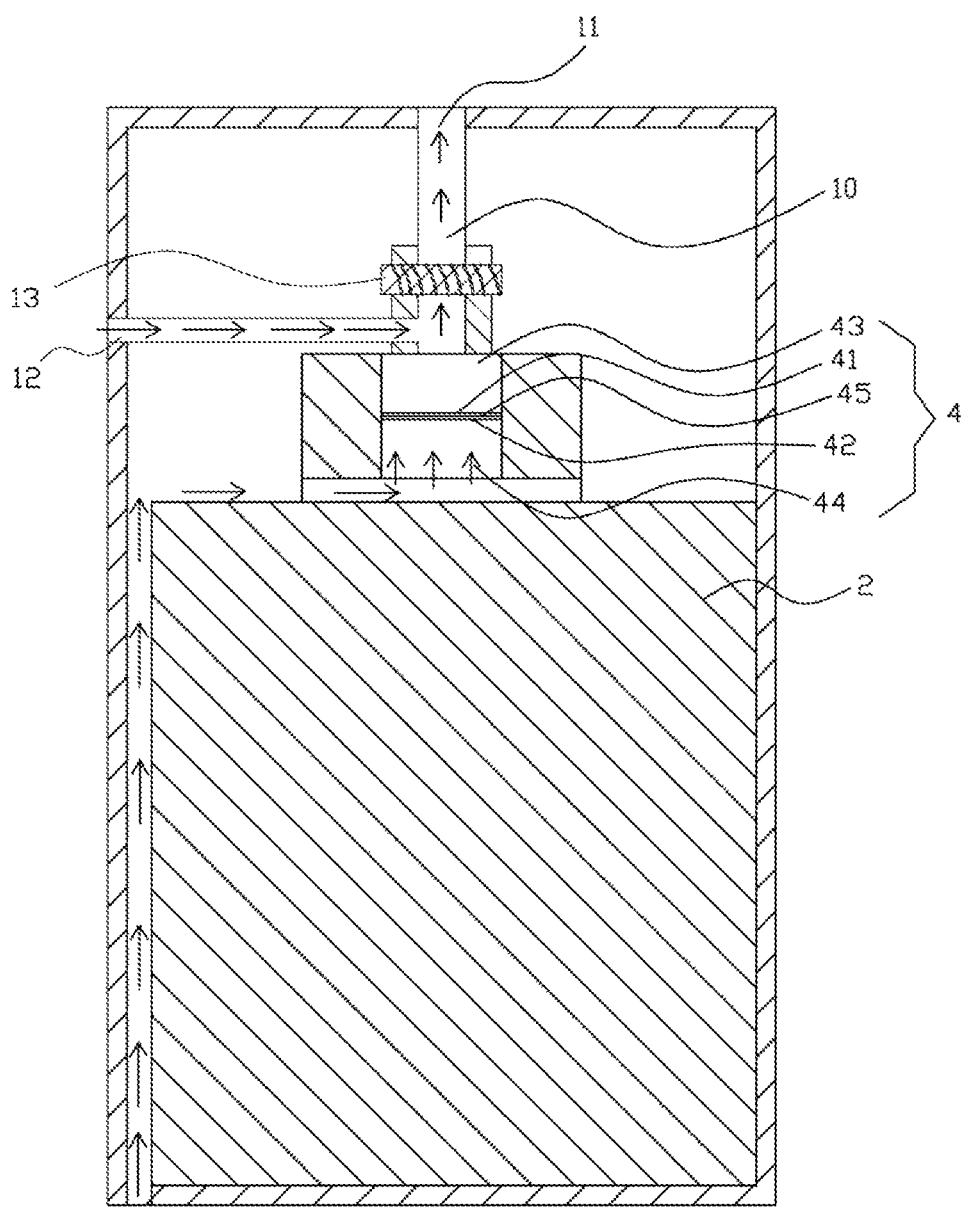
FIG. 5 is a cross-sectional view of the electronic cigarette according to a second embodiment of the present disclosure.
Figure 6:
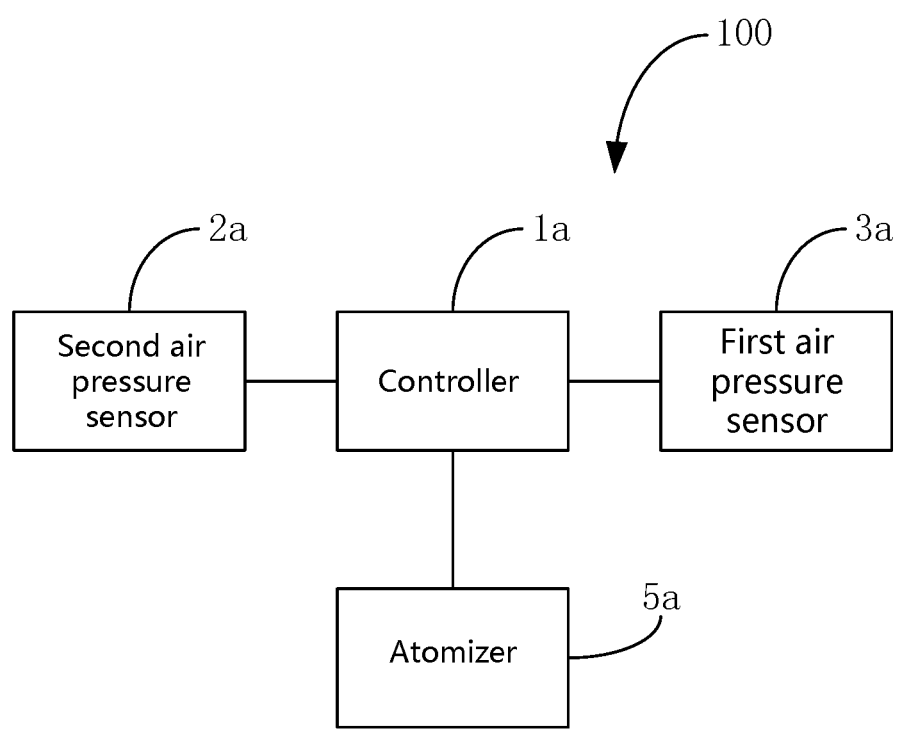
FIG. 6 is a block diagram of the electronic cigarette according to embodiments of the present disclosure.
Figure 7:
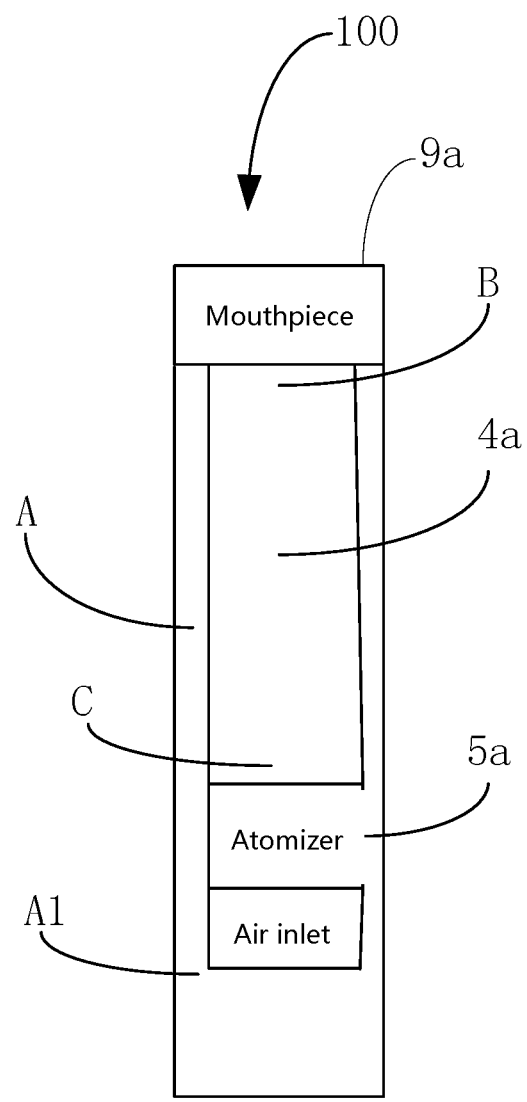
FIG. 7 illustrates the electronic cigarette according to another embodiment of the present disclosure.

As shown in FIG. 5, a block diagram of the electronic cigarette 100 according to a second embodiment of the present disclosure. The main differential compared to the embodiment 1, the air pressure sensor 4 in the electronic cigarette 100 has a measuring membrane 45, one side thereof has a first sensing surface 41, and the opposite side thereof has a second sensing surface 42. In some embodiments, a top side of the measuring membrane 45 has a first sensing surface 41, the opposite side thereof has a second sensing surface 42.

The air pressure sensor 4 has a first channel 43 and a second channel 44. The first channel 43 is in communication with the air flow path 10, making the first sensing surface 41 available of contacting the airflow in the air flow path 10 to detect the first air pressure in the air flow path 10. The second channel 44 is in communication with the ambient atmosphere of the electronic cigarette 100, making the second sensing surface 42 available of contacting the ambient atmosphere of the electronic cigarette 100 to detect the second air pressure in the ambient atmosphere. The air pressure sensor 4 feeds back the pressure differential between the second air pressure and the first air pressure to the controller 3, thus the controller 3 controls on/off of the atomizer 1 based on the pressure differential. The axis of the first channel 43 is perpendicular to the panel surface of the measuring membrane 45, the axis of the second channel 44 is perpendicular to the panel surface of the measuring membrane 45.

Understandable, in other embodiments, the first sensing surface 41 is in communication with the ambient atmosphere to detect the air pressure in the atmosphere. The second sensing surface 42 is in communication with the air flow path 10 to detect the air pressure in the air flow path 10.

Figure 8:
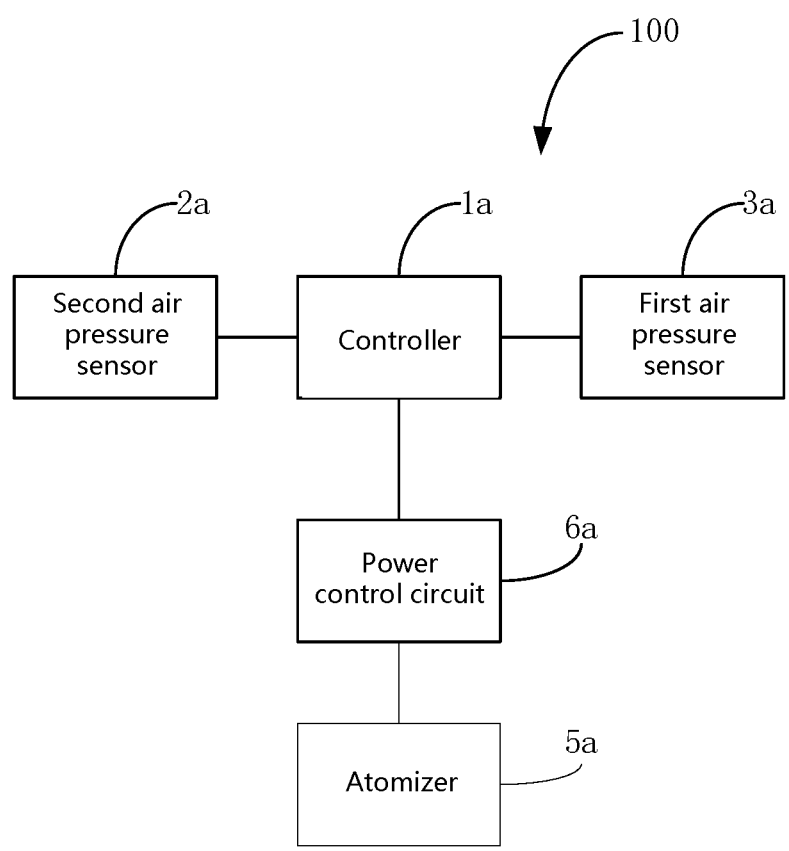
FIG. 8 is a block diagram of the electronic cigarette according to another embodiment of the present disclosure.

In the embodiment, the controller 3 receives the pressure differential between the second air pressure and the first air pressure transmitted from the air pressure sensor 4. And the controller 3 compares the pressure differential with the preset threshold vale arranged in the controller 3, if the pressure differential is greater than the threshold value, the controller 3 controls the atomizer 1 to be initiated; if the pressure differential is less than or equal to the threshold value, the controller 3 controls the atomizer 1 not to be initiated or to be closed.

Embodiment Three

Referring to FIGS. 6 and 7, which illustrate the electronic cigarette in accordance with two embodiments of the present disclosure. The electronic cigarette 100*a* includes a controller 1*a*, a second air pressure sensor 2*a* and a first air pressure sensor 3*a*.

In the present application, the second air pressure sensor 2*a* and the first air pressure sensor 3*a* are respectively coupled with the controller 1*a*. The second air pressure sensor 2*a* is disposed in the electronic cigarette 100*a* where is in communication with the ambient atmosphere to detect the second air pressure in the ambient atmosphere so as to transmit the second air pressure to the controller 1*a*. If applicable, the second air pressure sensor 2*a* on PCBA (which is an abbreviation of "printed circuit board assembly") is positioned near an air inlet. The first air pressure sensor 3*a* is disposed in the air flow path 4*a* of the electronic cigarette 100*a* to detect the first air pressure in the air flow path 4*a* and transmit the first air pressure to the controller 1*a*. If applicable, the first air pressure sensor 3*a* is one PCBA is positioned within the air flow path 4*a*. As described above, the controller 1*a* is configured for controlling the atomizer 5*a* in the electronic cigarette 100*a* to be initiated or closed.

In general, the air pressure sensor is an apparatus/device capable of monitoring signals of air pressure and regularly transforming the signals of air pressure to usable electrical signals that are outputted eventually. The second air pressure sensor 2*a* is configured to detect the second air pressure in the ambient atmosphere, thus the second air pressure sensor 2*a* is disposed at position A where is in communication with ambient atmosphere. The first air pressure sensor 3*a* is configured to detect the first air pressure in the air flow path 4*a* thus the first air pressure sensor 3*a* is disposed within the air flow path 4*a*. The pressure differential between the second air pressure and the first air pressure is represented the air pressure in ambient atmosphere deducting the air pressure in the air flow path 4*a*. Without any ambient forces, the second air pressure in the ambient atmosphere is basically the same as the first air pressure in the air flow path 4*a*, the differential is zero. When the pressure differential is more than zero, it indicates the second air pressure isn't the same as the first air pressure. In this case, given that a force with a positive or negative direction is applied to electronic cigarette 100*a* during users draw or blow the mouthpiece, when users draw, the force is positive, when users blow, the force is negative. When the second air pressure in the ambient atmosphere is greater than the first air pressure in the air flow path 4*a*, that is the pressure differential is greater than zero, it indicates the force is positive since the user is drawing the mouthpiece. When the second air pressure in the ambient atmosphere is less than the first air pressure in the air flow path 4*a*, that is the pressure differential is less than zero, it indicates the force is negative since the user is blowing air into the mouthpiece. As a result, the atomizer 5*a* is controlled by the controller 1*a* to be initiated or closed.

Basically, the pressure differential between the air pressure near the air inlet in the air flow path 4*a* and the other air pressure near in a position near the mouthpiece 9*a* in the air flow path 4*a* may accurately illustrate whether the user is drawing or blowing air from the electronic cigarette. In some embodiments, if applicable, the second air pressure sensor 2*a* is disposed at the position A1 near the air inlet and the first air pressure sensor 3*a* is at the position B disposed near the mouthpiece 9*a*.

In other embodiments, if applicable, the second air pressure sensor 2*a* is disposed at the position A1 near the air inlet and the first air pressure sensor 3*a* is at the position C disposed near the atomizer 5*a*.

The electronic cigarette of the present disclosure has a controller 1*a*, a second air pressure sensor 2*a* and a first air pressure sensor 3*a*. As used herein, the second air pressure sensor 2*a* is disposed in the electronic cigarette 100*a* where is in communication with the ambient atmosphere, configured to detect a second air pressure in the ambient atmosphere and further to transmit the second air pressure to the controller 1*a*. The first air pressure 3*a* is disposed in the air flow path 4*a* of the electronic cigarette 100*a* to detect the first air pressure in the air flow path 4*a* and further to transmit the first air pressure to the controller 1*a*. The controller 1*a* is configured for receiving the pressure differential between the second air pressure and the first air pressure and further controlling the on/off state of the atomizer 5*a* in the electronic cigarette 100*a*. Since the controller 1*a* in the electronic cigarette 100*a* controls the on/off state of the atomizer 5*a* according to the pressure differential there-between, the pressure differential may be consistent and controllable, not to be affected by the leaking tobacco liquid or condensed aerosol. By relying on this, the electronic cigarette 100*a* has a consistent sensibility and high reliability without false triggering or out of work.

In some embodiments, the controller 1*a* stores the preset threshold value. The controller 1*a* is configured as when the pressure differential is more than zero or more than a preset pressure differential, controlling the atomizer 5*a* to be initiated; when the pressure differential is equal to or less than the preset pressure differential, controlling the atomizer 5*a* not to be initiated or to be closed. Since the pressure differential between the second air pressure and the first air pressure has a deviation, for further making the atomizer 5*a* available for satisfying users' smoking demand. In the embodiment, a preset threshold value is provided beforehand, only when the pressure differential is greater than the threshold value, the atomizer 5*a* is initiated; when the pressure differential is equal to or less than the preset pressure differential, the atomizer 5*a* is controlled not to be initiated or to be closed, therefore avoiding deviation of the pressure differential to cause false triggering of the atomizer 5*a*.

The second air pressure is a real-time value detected in the ambient atmosphere; the first air pressure is real-time value detected in the air flow path, thus the pressure differential is a real-time value that may control the on/off state of the atomizer 5*a* immediately. That means, the controller 1*a* controls the atomizer 5*a* in the electronic cigarette 100*a* to be initiated or to be closed according to the pressure differential and the preset threshold value.

In some embodiments, the output power of the power supply set may be adjusted according to the pressure differential, thus the amount of aerosol may be adjusted. With reference to FIG. 8, the electronic cigarette 100a further includes a power control unit 6a coupled with the controller 1a. When the atomizer 5a is initiated, the controller 1a determines the real-time output power corresponding to the real-time detected pressure differential according to corresponding relationship between the pressure differentials and output powers, afterwards, the controller 1a transmits a first instruction to the power control circuit 6a, then the power control circuit 6a in response to the first instruction outputs real-time output power to the atomizer 5a, therefore the atomizer 5a generates a certain amount of aerosol that is corresponding to the real-time output power.

In the embodiment, during the invention process by the inventor, the corresponding relationship between the pressure differentials and the output powers, and the corresponding relationship between the output powers and the certain amount of aerosol are determined beforehand. In this case, the real-time output power may be determined according to the real-time detected pressure differential, the controller 1a transmits the first instruction to the power control circuit 6a. The power control circuit 6a in response to the first instruction outputs the real-time output power corresponding to the pressure differential, therefore the atomizer 5a may generate a certain amount of aerosol corresponding to the real-time output power.

For instance, above corresponding relationships hereto are determining beforehand: when 3 to 4 units of pressure differentials generated, 2 to 3 units of output powers outputted accordingly; when 5 to 6 units of pressure differentials generated, 4 to 5 units of output powers outputted accordingly; when 7 to 8 units of pressure differentials generated, 6 to 7 units of output powers outputted accordingly; when 9 to 10 units of pressure differentials, 8 to 9 units of output powers outputted accordingly. If the real-time detected pressure differentials are 4 units, 3 units of output powers are outputted accordingly. And if the real-time detected pressure differentials are 7 units, 6 units of output powers are outputted accordingly, and so on.

Furthermore, in the corresponding relationship therebetween, the greater pressure differential is corresponding to a greater output power, that means, a more amount of aerosol are generated by the atomizer, which may simulate and satisfy the user's actual demands for smoking, and user experience is improved.

In an embodiment, the electronic cigarette also may judge whether the user is drawing or blowing the electronic cigarette, which is beneficial for accurately controlling the on or off state of the atomizer. More specifically, the pressure differential is that the second air pressure deducts the first air pressure. The controller 1a is arranged as when the pressure differential is greater than zero, determining the direction of air flowing in the air flow path 4a is towards the mouthpiece, that is drawing the electronic cigarette, the atomizer 5a is initiated accordingly; when the pressure differential is less than zero, determining the direction of air flowing in the air flow path 4a is departing the mouthpiece, that is blowing the electronic cigarette, the atomizer 5a is not initiated or closed.

Figure 9:
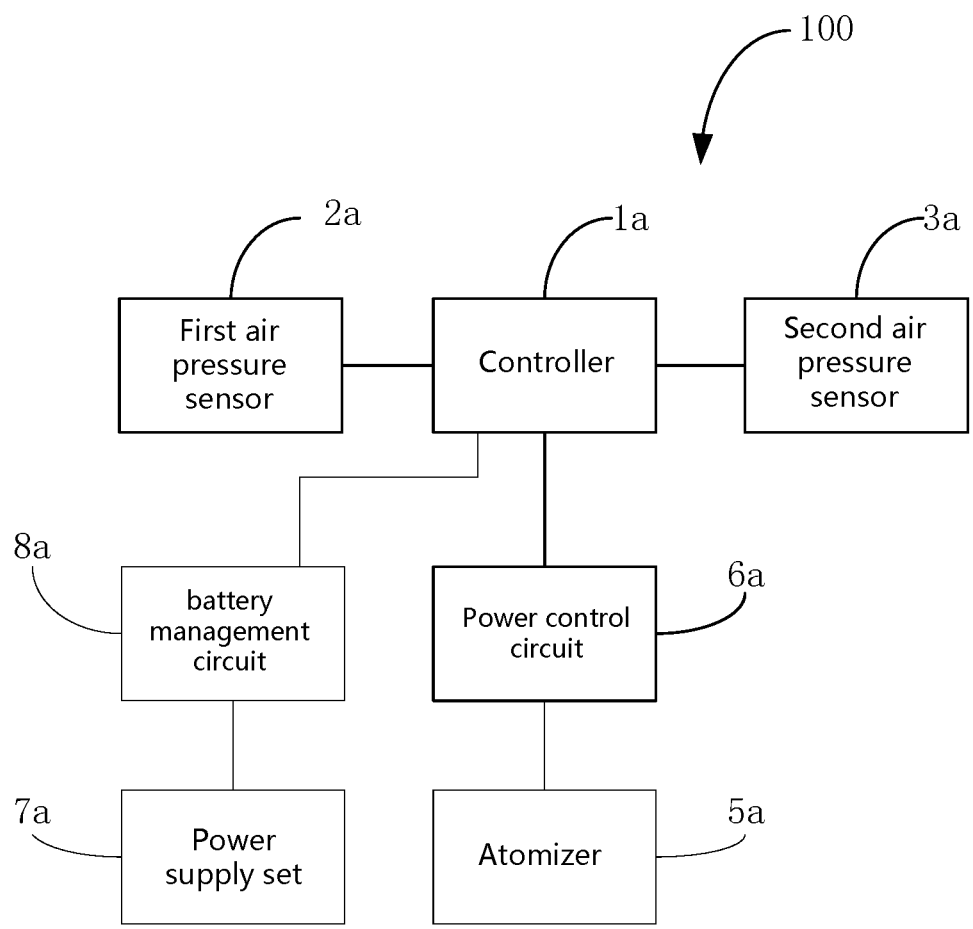
FIG. 9 is a block diagram of the electronic cigarette according to another embodiment of the present disclosure.

As shown in FIG. 9, in an embodiment, the electronic cigarette 100a further includes a battery management circuit 8a coupled with the controller 1a, the controller 1a is further configured for transmitting a second instruction to the battery management circuit 8a. The battery management circuit 8 responses to the second instruction to manage the power supply set 7a in electronic cigarette 100a.

Furthermore, the battery management circuit 8a is configured for charge management, discharge management and security monitoring and management on the power supply set 7a in the electronic cigarette 100a. In this embodiment, the power supply set 7a is a lithium-battery.

Figure 10:
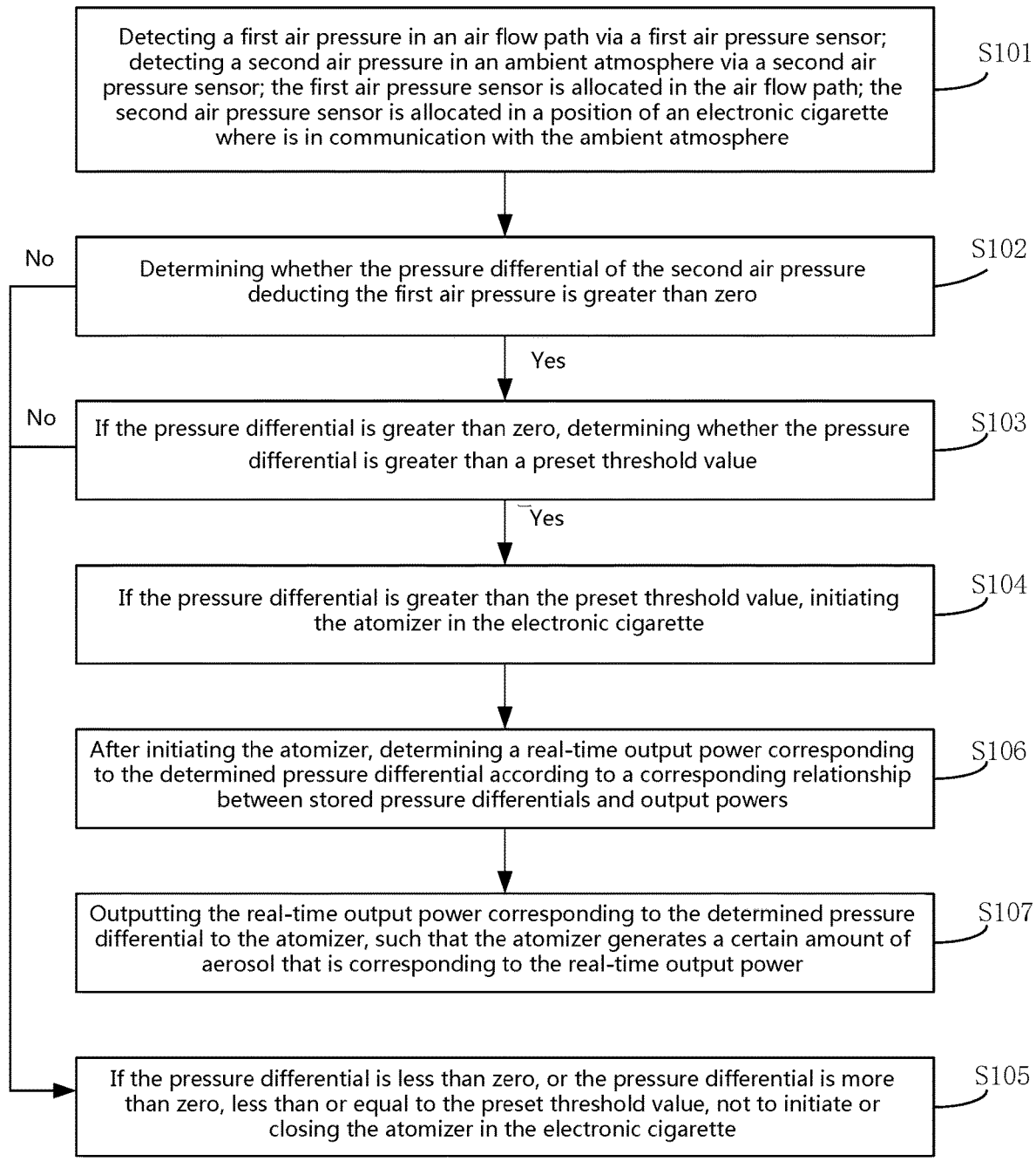
FIG. 10 is a flow chat of the control method for the electronic cigarette according to another embodiment of the present disclosure.

Referring to FIG. 10, which is a flow chat of the control method for the electronic cigarette according to another embodiment of the present disclosure. The control method is applied to the electronic cigarette as described above and relative content can be referred to the above description, not to state again. The control method includes:

S101: detecting the second air pressure in the ambient atmosphere of the electronic cigarette via the second air pressure sensor, detecting the first air pressure in the air flow path of the electronic cigarette; as used herein, the second air pressure sensor is disposed in the electronic cigarette where is in communication with the ambient atmosphere and the first air pressure is disposed in the air flow path of the electronic cigarette.

S102: detecting whether the pressure differential equal to the second air pressure deducting the first air pressure is greater than zero;

S103: If the pressure differential is greater than zero, next detecting where the pressure differential is greater than a preset threshold value;

S104: If the pressure differential is greater than the threshold value, initiating the atomizer of the electronic cigarette;

S105: If the pressure differential is less than the threshold value or the pressure differential is greater than zero, and less than or equal to threshold value, not to initiate or closing the atomizer.

Furthermore, after the S104, the method further includes

S106: after initiating the atomizer, determining a real-time output power corresponding to the real-time detected pressure differential according to the detected pressure differential and corresponding relationship between pressure differentials and output powers.

S107: outputting a real-time output power to the atomizer according to the detected pressure differential.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. An electronic cigarette comprising:
   a controller;
   an air pressure sensor coupled with the controller;
   wherein the air pressure sensor comprises a single measuring membrane, one side thereof having a first sensing surface, and the opposite side thereof having a second sensing surface;
   the air pressure sensor further comprises a first channel and a second channel, wherein the first channel is in communication with an air flow path, making the first sensing surface available of contacting an airflow in the air flow path to detect a first air pressure;
   wherein the second channel is in communication with an ambient atmosphere, making the second sensing surface available of contacting a second air pressure;
   wherein the controller is configured for receiving the second air pressure and the first air pressure and controlling an atomizer to be on or off based on a pressure differential between the first air pressure and the second air pressure;

wherein the pressure differential is equal to that the second air pressure deducts the first air pressure;

wherein a power control circuit is coupled with the controller and according to the pressure differential the power control circuit is capable of determining a real-time output power and wherein the controller gives instructions to the power control circuit, and the power control circuit in response to the instructions outputs a real-time output power to the atomizer.

2. The electronic cigarette according to claim 1, wherein the controller is provided with a threshold value; the controller is configured as: when the pressure differential is greater than the threshold value controlling the atomizer to be initiated, and when the pressure differential is less than or equal to the threshold value controlling the atomizer not to be initiated or to be closed.

3. The electronic cigarette according to claim 1, wherein, in the corresponding relationship between the pressure differentials and the real-time output powers, the greater pressure differential is corresponding to the greater real-time output power.

4. The electronic cigarette according to claim 1, wherein the controller is configured as: when the pressure differential is more than zero, determining the airflow in the air flow path is flowing outside from an aerosol outlet with consequently controlling the atomizer to be initiated; when the pressure differential is less than zero, determining the airflow in the air flow path is flowing inside from the aerosol outlet with consequently controlling the atomizer not to be initiated or to be closed.

5. The electronic cigarette according to claim 1, further comprising:
a power supply set having a rechargeable battery; and
a power reminder unit coupled with the controller;
when the rechargeable battery runs out of charge, the power reminder unit is capable of reminding to supply power to the rechargeable battery.

6. The electronic cigarette according to claim 5, wherein the power reminder unit is an indicator light; when the rechargeable battery runs at different reminding capacities, the controller is capable of controlling the indicator light to generate different colors.

7. An electronic cigarette comprising:
a controller; and
an air pressure sensor coupled with the controller;
wherein the air pressure sensor comprises a first measuring membrane and a second measuring membrane, both membranes encompassing a single chamber, that is closed by the two membranes;
wherein a first sensing surface is arranged on a first side of the first measuring membrane outside a closed chamber; a second sensing surface is arranged on a second side of the second measuring membrane outside the closed chamber;
wherein the air pressure sensor further comprises a first channel, a second channel, the first sensing surface being arranged within the first channel and the second sensing surface being arranged within the second channel, the first channel being in communication with an air flow path;
wherein the second channel is in communication with an ambient atmosphere of the electronic cigarette; wherein a first air pressure in the air flow path is detected via the first sensing surface, which faces a direction of the air flow path and
wherein a second air pressure of the ambient atmosphere is detected via the second sensing surface, which faces a direction of the ambient atmosphere path; and
wherein the air pressure sensor being configured for feeding back a pressure differential between the second air pressure and the first air pressure to the controller; the controller capable of controlling an on or off state of an atomizer according to the pressure differential
wherein the pressure differential is equal to that the second air pressure deducts the first air pressure;
wherein a real-time output power corresponding to the pressure differential is determined and outputted to the atomizer.

* * * * *

UNITED STATES PATENT AND TRADEMARK OFFICE
CERTIFICATE OF CORRECTION

PATENT NO. : 11,660,405 B2
APPLICATION NO. : 16/443894
DATED : May 30, 2023
INVENTOR(S) : Yan et al.

It is certified that error appears in the above-identified patent and that said Letters Patent is hereby corrected as shown below:

On the Title Page

Item (30), Please add as follows:
Nov. 9, 2018 (CN) 201811329295.1

Signed and Sealed this
Fifth Day of September, 2023

Katherine Kelly Vidal
*Director of the United States Patent and Trademark Office*